US009827443B2

(12) United States Patent
van Erp et al.

(10) Patent No.: US 9,827,443 B2
(45) Date of Patent: Nov. 28, 2017

(54) MODULAR APPLICATOR FOR BRACHYTHERAPY

(71) Applicant: Nucletron Operations B.V., Veenendaal (NL)

(72) Inventors: Wilhelmus Petrus Martinus Maria van Erp, Veenendaal (NL); Tommy Robert Oscar Martens, Veenendaal (NL); Gaetan Stephan Marie van Wijck, Veenendaal (NL); Cor van de Wardt, Veenendaal (NL)

(73) Assignee: Nucletron Operations B.V., Veenendaal (NL)

( * ) Notice: Subject to any disclaimer, the term of this patent is extended or adjusted under 35 U.S.C. 154(b) by 290 days.

(21) Appl. No.: 14/063,527

(22) Filed: Oct. 25, 2013

(65) Prior Publication Data

US 2014/0121444 A1  May 1, 2014

Related U.S. Application Data

(60) Provisional application No. 61/718,403, filed on Oct. 25, 2012.

(30) Foreign Application Priority Data

Oct. 25, 2012  (NL) .................................... 2009697

(51) Int. Cl.
*A61N 5/00* (2006.01)
*A61N 5/10* (2006.01)
*A61M 25/02* (2006.01)

(52) U.S. Cl.
CPC ..... *A61N 5/1016* (2013.01); *A61M 2025/028* (2013.01); *A61N 5/1007* (2013.01);
(Continued)

(58) Field of Classification Search
CPC .......... A61N 5/1016; A61N 2005/1018; A61N 2005/0611; A61N 5/1014; A61N 5/1015;
(Continued)

(56) References Cited

U.S. PATENT DOCUMENTS 4,331,131 A * 5/1982 Kumar ................. A61N 5/1016
600/6
4,554,909 A 11/1985 Pino Y Torres
(Continued)

FOREIGN PATENT DOCUMENTS

EP         1854507 A1    11/2007
WO    WO 2007/149578 A2    12/2007
(Continued)

OTHER PUBLICATIONS

International Search Report and Written Opinion for International Application No. PCT/NL2013/050750, dated May 16, 2014 (15 pages).
(Continued)

*Primary Examiner* — Charles A Marmor, II
*Assistant Examiner* — Shannon McBride
(74) *Attorney, Agent, or Firm* — Bookoff McAndrews, PLLC

(57) ABSTRACT

A modular applicator for enabling a brachytherapy treatment comprising a central element and one or more of peripheral elements, wherein the central element is adapted with a fixation mechanism having a core for affixing the said peripheral elements thereto, wherein the fixation mechanism prevents a rotational displacement of the peripheral elements attached to the core of the fixation element with respect to the central element.

33 Claims, 6 Drawing Sheets

(52) U.S. Cl.
CPC .......... *A61N 5/1014* (2013.01); *A61N 5/1015* (2013.01); *A61N 5/1027* (2013.01); *A61N 2005/1008* (2013.01); *A61N 2005/1009* (2013.01); *A61N 2005/1018* (2013.01)

(58) Field of Classification Search
CPC .......... A61N 5/1007; A61N 2005/1009; A61N 5/1027; A61N 2005/1008; A61N 2005/1011; A61M 2025/028
See application file for complete search history.

(56) References Cited

U.S. PATENT DOCUMENTS

| | | | |
|---|---|---|---|
| 6,390,968 B1* | 5/2002 | Harmon | 600/6 |
| 6,676,590 B1* | 1/2004 | Urick et al. | 600/3 |
| 2004/0073088 A1* | 4/2004 | Friedman et al. | 600/114 |
| 2010/0048978 A1* | 2/2010 | Sing et al. | 600/6 |
| 2011/0257459 A1 | 10/2011 | Sutton et al. | |
| 2012/0029263 A1* | 2/2012 | Wardt et al. | 600/7 |
| 2012/0123188 A1* | 5/2012 | Rahimian | 600/6 |
| 2013/0317276 A1* | 11/2013 | D'Andrea | 600/2 |
| 2014/0005539 A1* | 1/2014 | Forster et al. | 600/431 |

FOREIGN PATENT DOCUMENTS

| | | |
|---|---|---|
| WO | WO 2007149578 A2 * | 12/2007 |
| WO | WO 2013/177249 A1 | 11/2013 |

OTHER PUBLICATIONS

Response to Written Opinion for International Application No. PCT/NL2013/050750, dated Aug. 25, 2014 (3 pages).
Second Written Opinion for International Application No. PCT/NL2013/050750, dated Nov. 11, 2014 (8 pages).
Response to Second Written Opinion for International Application No. PCT/NL2013/050750, dated Jan. 9, 2015 (5 pages).
International Preliminary Report on Patentability for International Application No. PCT/NL2013/050750, dated Mar. 12, 2015 (9 pages).

* cited by examiner

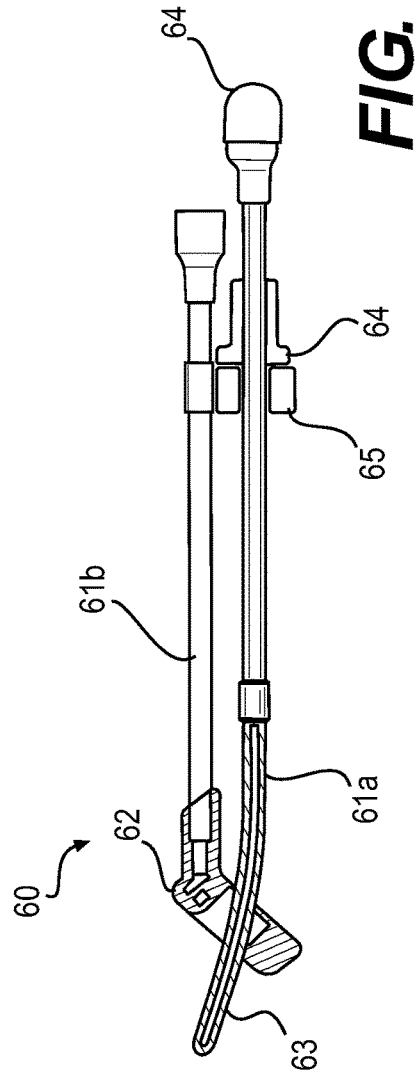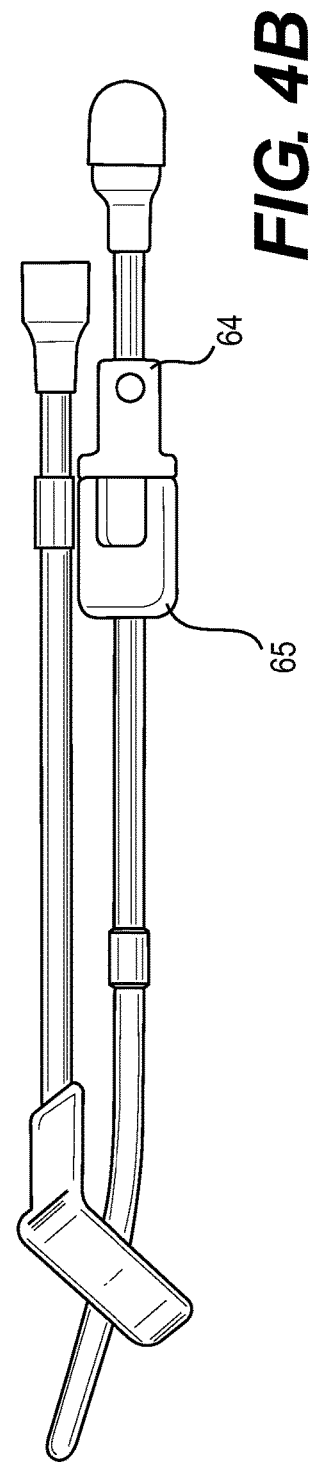

MODULAR APPLICATOR FOR BRACHYTHERAPY

PRIORITY

This patent application claims the benefit of priority under 35 U.S.C. §120 to U.S. Provisional Application No. 61/718,403, filed on Oct. 25, 2012, the entirety of which is incorporated herein by reference. This patent application also claims the benefit of priority under 35 U.S.C. §119 to The Netherlands Patent Application No. 2009697, filed on Oct. 25, 2012, which is incorporated herein by reference in its entirety.

FIELD OF THE INVENTION

The invention relates to a modular applicator for brachytherapy.

BACKGROUND OF THE INVENTION

Cancers, having increased incidence rate in the last decade of the 20$^{th}$ century, require substantial effort from medical professionals in terms of early diagnosis, logistics and availability of suitable treatment. However, it is appreciated that over 1.3 million new (skin) cancers are diagnosed annually and are increasing at a rate of about 5% per year.

Non proliferated cancers, being substantially superficial lesions, may be treated in different ways. First, surgery may be envisaged. However, such technique may be disadvantageous in terms of long waiting lists and complications related to post-treatment care. In addition, due to invasive character of surgery contamination of the wound by infections may present an additional risk. Secondly, external irradiation using electrons or electromagnetic radiation may be envisaged. Such techniques have a disadvantage that the patient has to receive about 25-30 fractions, which may be complicated for less mobile patients. In addition, irradiation of healthy tissues as well as reproducibility of the external beams with respect to the movable target may be a challenge.

Brachytherapy may provide an attractive compromise, wherein the radioactive sources are delivered inside the patient using applicators, either interstitially or intracavitary. Usually, a medical professional employs a standard applicator for treating different patients. However, due to difference in local anatomies the standard applicator may be not always an optimal solution for matching the patient geometry and for providing a pre-planned dose distribution inside the patient. Embodiments of the standard applicators are known from Nucletron, Applicator guide, Company Brochure, 2011.

Recently, it has been attempted to provide a customizable applicator, which may be composed of modules. An embodiment of a modular applicator is known from US 2011/0257459. In the known modular applicator a stack of longitudinal segments is provided, wherein the segments may be coupled to each other using suitable cooperating surfaces. Each segment is provided with a plurality of passages for providing a set of customizable channels for insertion of a radioactive source. A tip of the stack of segments may comprise one or more alignment notches, which may help define a certain orientation between the tip and a distal stacking component.

It is a disadvantage of the known modular applicator that it insufficiently provides the orientational certainty to the handling medical specialist. In particular, the stack of the segments having a number of pre-selected paths for the radioactive source may accidentally rotate about the central axis, which may lead to errors in dose delivery.

SUMMARY OF THE INVENTION

It is an object of the invention to provide an improved modular applicator for brachytherapy. In particular, it is an object of the invention to provide a modular applicator which is robust with respect to the pre-selected 3D orientation.

To this end the modular applicator for enabling a brachytherapy treatment according to an aspect of the invention comprises a central element and one or more of peripheral elements, wherein the central element is adapted with a fixation mechanism having a core for affixing the said peripheral elements thereto, wherein the fixation mechanism prevents a rotational displacement of the peripheral elements attached to the core with respect to the central element.

It is found that by providing a unique mounting position for the peripheral elements, such as ovoids, it is possible to maintain the pre-determined 3D orientation of the applicator as a whole. In particular, it is found advantageous when the peripheral elements are mounted on a specifically designed fixation mechanism, which is provided on the central element. It will be appreciated, that particularly for the gyneacological applications, the central element, such as the intra-uterine tube, defines the axis for the dose delivery pattern. Therefore, by providing the fixation mechanism having non alterable pre-defined orientation for mounting the peripheral elements, a stable mechanical 3D construction may be provided. In an embodiment of the applicator according to a further aspect of the invention the fixation mechanism comprises a pre-oriented slot. This embodiment will be discussed in more details with reference to FIGS. 1a and 1b.

In an embodiment of the applicator according to a further aspect of the invention the fixation mechanism is rigidly connected to the central element.

It is found that although the fixation mechanism may be displaceable with respect to the central element, for example it may be slidable, it is advantageous to ensure that once the position of the fixation mechanism is set, it does not move. For example, the fixation mechanism may be embodied as a ring-like structure having an opening which substantially matches the diameter of the central element which protrudes through the opening. Preferably, the fixation mechanism is allowed to clamp In a further embodiment of the applicator according to a still further aspect of the invention, the fixation mechanism comprises a pre-oriented substantially cylindrical core adapted to be affixed on the central element.

It is found to be particular advantageous to provide the fixation element as a substantially elongated structure. This has an advantage that the mechanical rigidity of the application may be improved. Further details on this embodiment are given with respect to FIG. 5.

In a still further embodiment of the modular applicator according to an aspect of the invention, the central element comprises a plurality of substantially cylindrical conduits.

It is found to be advantageous to provide a number of independent conduits inside the central element for purposes of dose delivery. In particular, the substantially cylindrical conduits may be diverging from or converging to the central axis of the modular applicator. Accordingly, due to the fact that the peripheral elements contributing to the dose delivery pattern, are affixedly coupled to the central element, errors in dose delivery due to a human factor may be reduced.

In a still further embodiment of the modular applicator according to an aspect of the invention, the central element, being implemented as a central core is adapted to cooperate with an outer sleeve.

This embodiment is found to be particularly advantageous when an elongated, peer-shaped dose distribution pattern is required. The shape of the outer sleeve may be customized. For example, the outer sleeve may be shapeable for matching the local anatomy of the patient. In a particular embodiment the sleeve may be inflatable. For example the sleeve may be provided with a compartment having foam particles, which may be shaped under evacuation of the compartment using a suitable pump. This handling may be advantageously carried out prior to inserting the applicator inside the patient. In a further particular embodiment of the applicator, at least a portion of the outer surface of the sleeve is irregular. It is found to be particularly advantageous to provide the said portion of the outer surface with a set of local depletions. It is found that when the applicator is provided with an irregular surface (having bumps or depletions) it may be reliably maintained within a suitable cavity, such as vagina or rectum due to interaction of the patient's tissues with the irregular surface. In a particular embodiment of the application, the sleeve is transparent. This feature is found to be particularly useful for enabling reliable handling and mounting of the applicator. Still preferably, the applicator is provided with a suitable plurality of customized sleeves. For example, the sleeves may have different longitudinal or cross-sectional dimensions. In a still further embodiment, the customized sleeves are adapted to be manufactured in vivo. For example, the sleeves may be manufactures from a shapeable material, such as foam, settable polymer, or the like. Preferably, at least a proximal portion of the customized sleeves is shapeable. This feature is found to be particularly advantageous for customizing the form and shape of the ovoids used with the gynecological applicator. In a still further particular embodiment of the modular applicator, the proximal portion of the sleeve is provided with sub-portions capable of lateral displacement with respect to each other, whereas the applicator may comprise an indicator for indicating a value related to said displacement. This embodiment is discussed in more detail with reference to FIGS. 6a and 6b.

In a still further embodiment the sleeve may be modular. For example, the sleeve may comprise at least two modules in a longitudinal or in a transverse direction. It will be appreciated that in this case the sleeves may be provided with interlocks for keeping the stack of modules in the pre-defined position with respect to the central element.

In a still further embodiment, the cross-section of the sleeve may be modulated along the longitudinal direction of the sleeve. In particular, it is found that the outer sleeve may have different cross-sections along its length. This feature has an advantage of an improved dose delivery control.

In a still further embodiment of the applicator according to the invention, the core of the fixation mechanism is adapted with one or more lateral elements, wherein the said one or more lateral elements are rotatively displaceable with respect to the core of the fixation mechanism.

It is found to be advantageous to provide the modular applicator with a possibility to enable off-axis rotary displacement of the peripheral elements with respect to the longitudinal axis of the central element. This embodiment is discussed in more detail with reference to FIG. 7.

These and other aspects of the invention will be discussed with reference to drawings wherein like reference numerals or signs relate to like elements. It will be appreciated that the drawings are presented for illustration purposes only and may not be used for limiting the scope of the appended claims.

BRIEF DESCRIPTION OF THE DRAWINGS

FIG. 1b presents a further view of the embodiment shown in FIG. 1a.

FIG. 2b presents in a schematic way a further view of the applicator shown in FIG. 2a.

FIG. 3b presents a further view of the embodiment shown in FIG. 3a.

FIG. 4a presents in a schematic way a still further embodiment of the modular applicator provided with a fixation mechanism.

FIG. 4b presents in a schematic way a further view of the embodiment shown in FIG. 4a.

FIG. 6b presents a further view of the embodiment shown in FIG. 6a.

DETAILED DESCRIPTION OF THE DRAWINGS

Figure 1A:
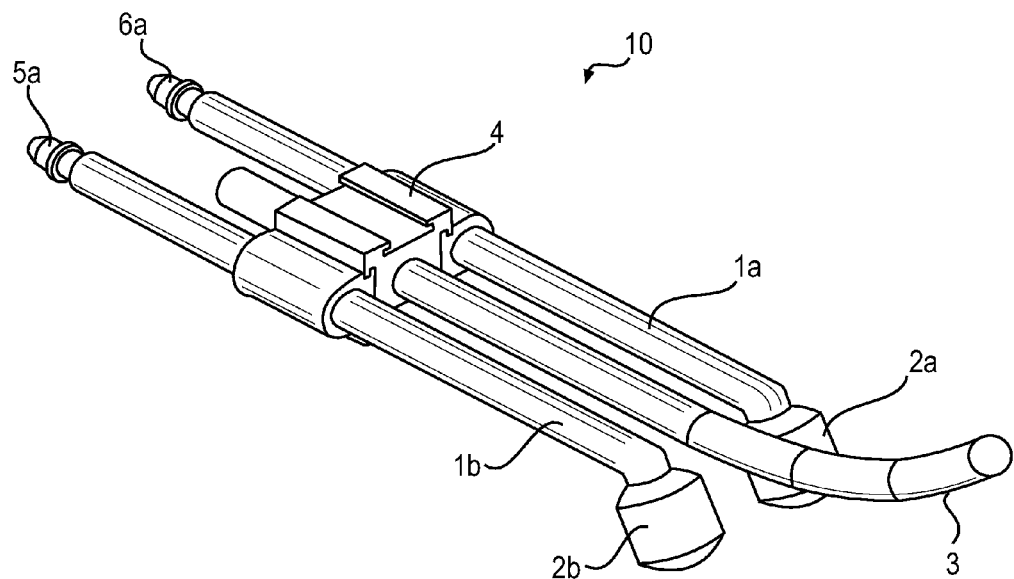
FIG. 1a presents in a schematic way an embodiment of the modular applicator provided with a fixation mechanism in the form of a slot.

FIG. 1a presents in a schematic way an embodiment of the modular applicator 10 provided with a fixation mechanism in the form of a slot. In the present embodiment the central element comprises two source guides 1a, 1b, whereon the fixation mechanism having a core 4 is affixed. The guides 1a, 1b are substantially tubular. The fixation mechanism comprises one or more suitably formed surfaces for enabling attachment of the peripheral elements. For example, the surfaces may have a shape of the guides arranged to cooperate with a mating guide of the peripheral element (not shown). In this way, the peripheral element may be slid on the fixation mechanism 4. The guides may have a shape of a slot or a rib. Alternatively, the peripheral elements may be attached to the core 4 by means of a snap fit, a seal ring or a bayonet joint, for example. The applicator 10 further comprises two ovoids 2a, 2b and an inter-uterine tube 3. The applicator 10 may be connected to a suitable afterloading device by the connectors 5a, 6a. It will be appreciated that the connectors 5a, 6a may be specifically designed to allow passage of a radioactive source. Suitably, the connectors (ports) 5a, 6a are provided on the proximal portion of the applicator 10.

The applicator 10 further comprises two ovoids 2a, 2b and an inter-uterine tube 3. The applicator 10 may be connected to a suitable afterloading device by the connectors 5a, 6a. It will be appreciated that the connectors 5a, 6a may be specifically designed to allow passage of a radioactive source. Suitably, the connectors (ports) 5a, 6a are provided on the proximal portion of the applicator 10.

It will be further appreciated that because the fixation mechanism 4 firmly holds the guides 1a, 1b, the guides maintain the inter-guide distance. Accordingly, the ovoids 2a, 2b do not displace with respect to each other.

Figure 1B:
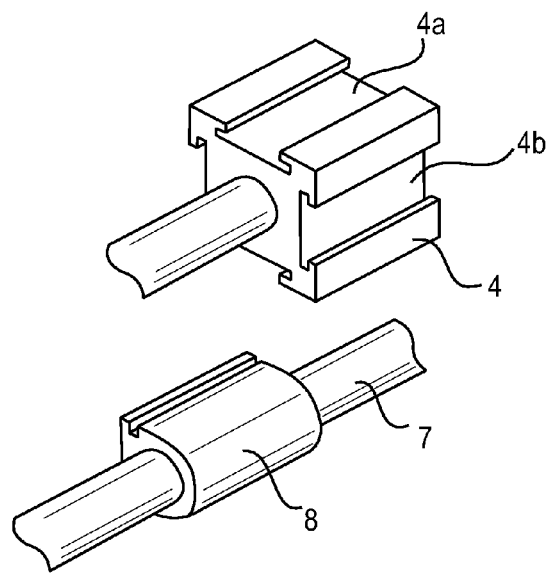

FIG. 1b presents a further view of the embodiment shown in FIG. 1a. In this embodiment the fixation mechanism 4 shown in FIG. 1a is depicted in more detail. It is seen that the fixation mechanism comprises surfaces 4a, 4b which are suitably shaped to allow connection to a peripheral element. An embodiment of a peripheral element which may be connected to such fixation mechanism is a rectal spacer, or a bladder spacer, for example.

Alternatively, the tubular guide 7 may be provided with a smaller fixation mechanism 8, which may have guiding slot surfaces only on one side. Those skilled in the art would readily appreciate that the shape of the fixation mechanism and the guiding surfaces shown in FIGS. 1a, 1b is not limiting. Various modifications of the fixation mechanism may be envisaged without departing from the scope of the invention.

Figure 2A:
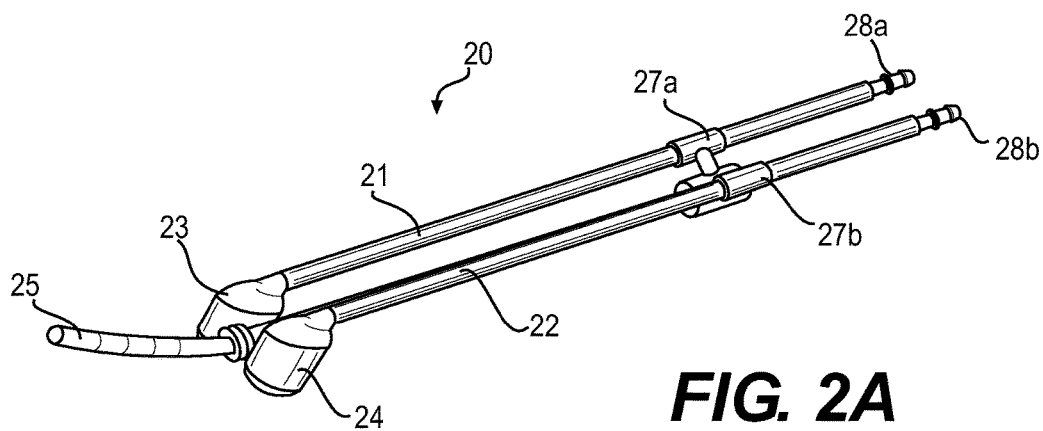
FIG. 2a presents in a schematic way a further embodiment of the modular applicator provided with a fixation mechanism.

FIG. 2a presents in a schematic way a further embodiment of the modular applicator provided with a fixation mechanism. In this particular embodiment a still further implementation of an aspect of the invention is provided. The central elements 21, 22 are interconnected using the fixation mechanism 27a, 27b which are provided with suitable slots or other fixation means for attaching peripheral elements. The guides 21, 22 may communicate with the afterloader device using the ports 28a, 28b. The ovoids 23, 24 are provided distally from the central elements together with the intra-uterine tube. It will be appreciated that because the central elements are affixed to each other by the fixation mechanism, a stable mechanical configuration is achieved which does not allow for rotational degree of freedom.

Figure 2B:
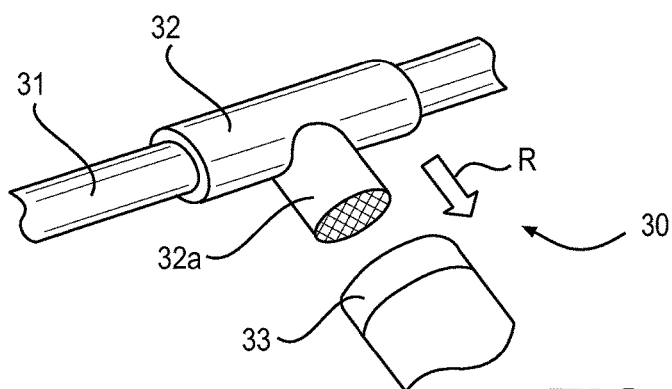

FIG. 2b presents in a schematic way a further view of the applicator shown in FIG. 2a. In this view a close-up on the fixation mechanism shown with respect to the central element 31. The fixation mechanism 32 may be glued to the central element, or may be provided on it using different means. A suitable peripheral element 33, may be clicked on a projection 32a provided on the fixation mechanism 32. The peripheral element may be detached in the directions schematically shown by arrow R. Also this configuration allows for a stable construction of the applicator 30, which does not allow for a rotational degree of freedom.

Figure 2C:
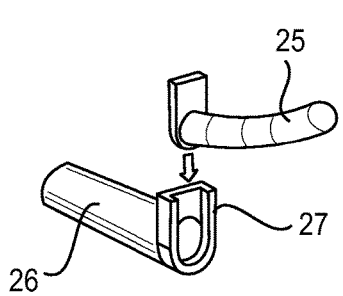
FIG. 2c presents in a schematic view a further embodiment of the fixation mechanism.
Figure 2D:
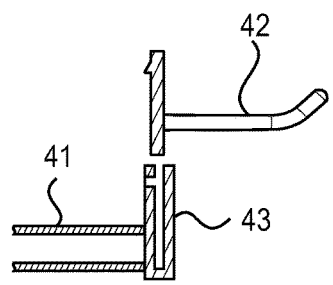
FIG. 2d presents in a schematic view a cross-section of the embodiment shown in FIG. 2c.

FIG. 2c presents in a schematic view a further embodiment of the fixation mechanism. In this particular embodiment the intra-uterine tube 25 serves as a central element. A suitable fixation mechanism 26 may be suitably attached to the intra-uterine tube 25. FIG. 2d presents in a schematic view a cross-section of the embodiment shown in FIG. 2c. Although in this particular embodiment a snap fit connection is shown, those skilled in the art would readily appreciate that any other mechanical connection is possible.

Figure 3A:
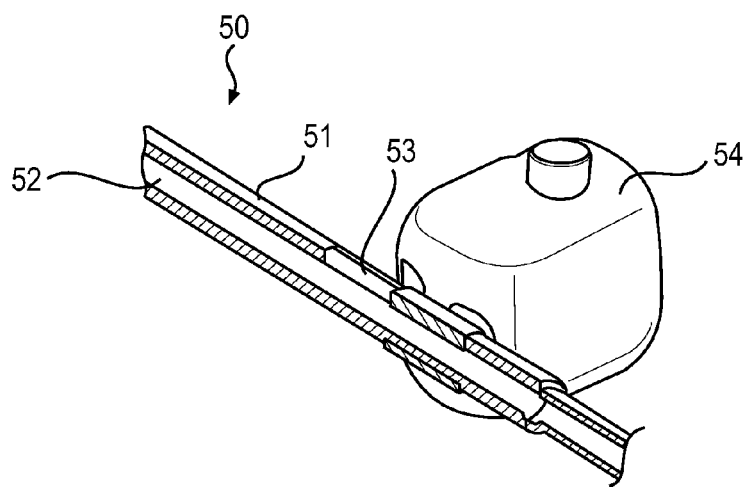
FIG. 3a presents in a schematic way a still further embodiment of the modular applicator provided with a fixation mechanism.

FIG. 3a presents in a schematic way a still further embodiment of the modular applicator 50 provided with a fixation mechanism. In this particular embodiment the central element 51 is tubular, having an inner opening 52 through which a suitable radioactive source may be transported during treatment or maintenance. A fixation mechanism 53 is firmly attached to the central element 51. A peripheral element 54 (an ovoid) is attached to the fixation element 53 by means of a suitable connection (not shown).

Figure 3B:
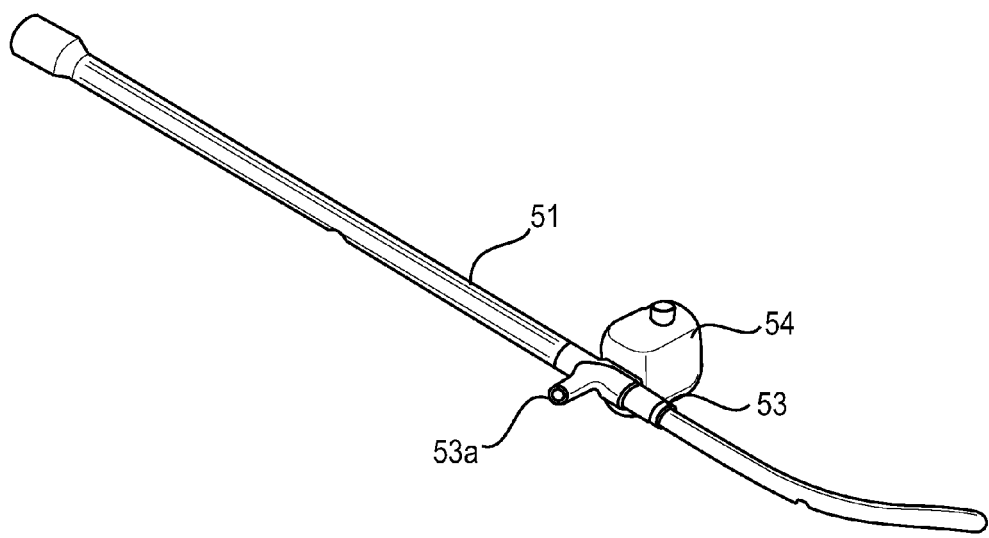

It will be appreciated that various connections are possible—guiding slots, snap fits and so on are contemplated. In FIG. 3b presenting a further view of the embodiment shown in FIG. 3a it is seen that the fixation element 53 may comprise a suitable projection 53a for connection of further peripheral elements thereto. For example, a second ovoid may be connected in this way to the fixation mechanism 53.

This embodiment has an advantage that the peripheral elements (ovoids) do not have any rotational degree of freedom with respect to the central element 51 thereby improving accuracy of dose delivery.

FIG. 4a presents in a schematic way a still further embodiment of the modular applicator provided with a fixation mechanism. The applicator 60, schematically shown in cross-section, comprises a central element 61a, 61b, wherein the fixation mechanism 64 is connected to the central element 61a. The port 64 is used for connecting to an afterloading device. The central element 61b is connected to a ring portion 62 which is also used for dose delivery. FIG. 4b presents in a schematic way a three-dimensional view of the embodiment shown in FIG. 4a. The fixation mechanism 64 may be implemented as a fixation nut 64 cooperating with a universal connection block 65.

Figure 5:
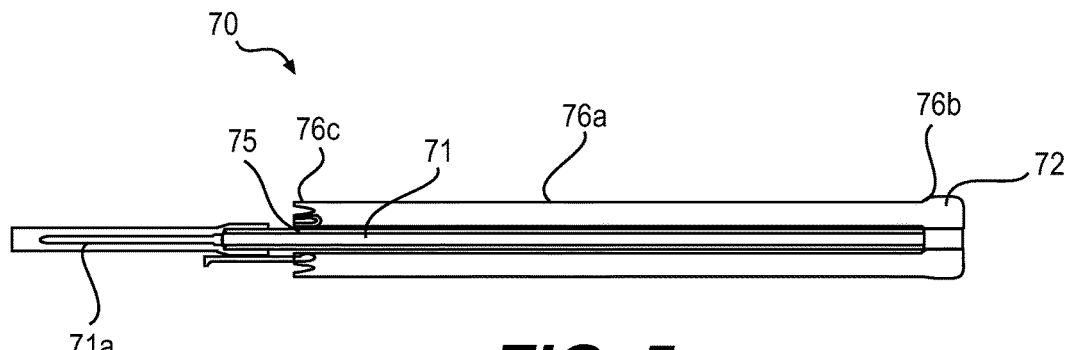
FIG. 5 presents in a schematic way a still further embodiment of the modular applicator provided with a fixation mechanism.

FIG. 5 presents in a schematic way a still further embodiment of the modular applicator provided with a fixation mechanism. In the present embodiment the modular applicator 70 comprises a central element 71 having a proximal end 71a. On the central element a fixation mechanism 75 is provided on top of which a substantially cylindrical shell 76a is provided. The fixation mechanism may be implemented in accordance with the foregoing. The proximal portion 76b of the shell 76a comprises a regulator 72. For example, the regulator 72 may relate to a rotational knob, which is arranged to alter the diameter of the distal portion 76c of the shell. Accordingly, the distal portion of the applicator 70 may be shapeable on demand.

Figure 6A:
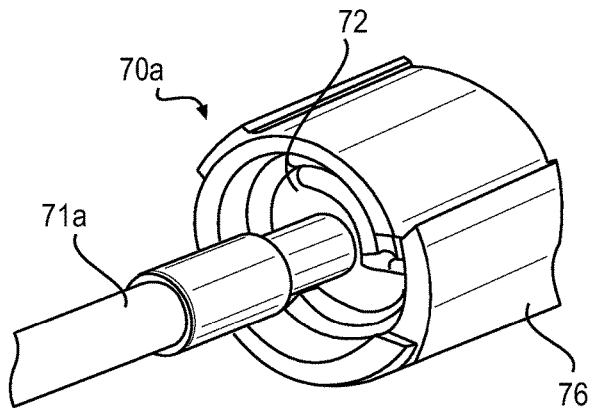
FIG. 6a presents in a schematic way an embodiment of the modular applicator having shapeable proximal end.

FIG. 6a presents in a schematic way an embodiment of the modular applicator having shapeable proximal end. In this view a proximal end of the applicator 70a is shown in three-dimensions. Accordingly, on the central element 71a an outer shell (or sleeve) is affixed using a suitable fixation element (not shown). The proximal portion of the applicator 70a comprises a rotatable knob 72 which influences a dimension of the shell 76 along its length. Although in a preferred embodiment only the distal dimension of the shell may be altered, it is possible to provide a plurality of actuatable portions on the shell for modifying the diameter locally.

Figure 6B:
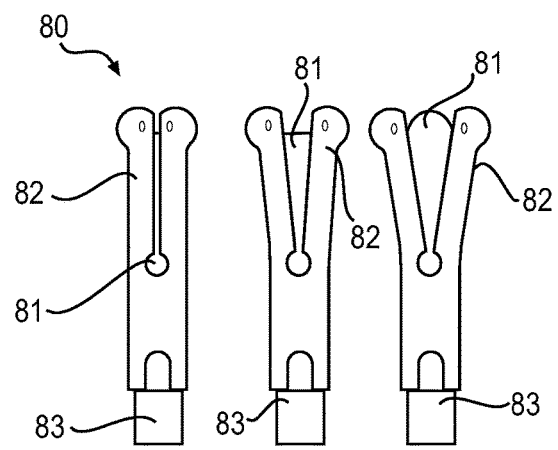

FIG. 6b presents a further view of the embodiment shown in FIG. 6a.

In this embodiment a further way of modifying the proximal portion is depicted. The modular applicator 80 according to an aspect of the invention comprises a central portion onto which an outer shapeable sleeve is attached using a suitable fixation mechanism (not shown). The applicator 80 further comprises an actuator 83, which is adapted to modify the shape and/or dimension of the proximal portion of the applicator. For example, the proximal portion may comprise a number of sub-portions. By means of the actuator 83, the distance between the sub-portions may be modified. Preferably, the displacement of the sub-portions with respect to each other is calibrated. The actuator may suitably comprise an indicator for indicating to the user to which degree the sub-portions are displaced from each other.

This embodiment has an advantage in that next to maintaining the prescribed 3D orientation of the applicator, it is possible to shape it in use. Accordingly, the accuracy of the dose delivery may be still further improved with respect to the applicators known from the prior art.

Figure 7:
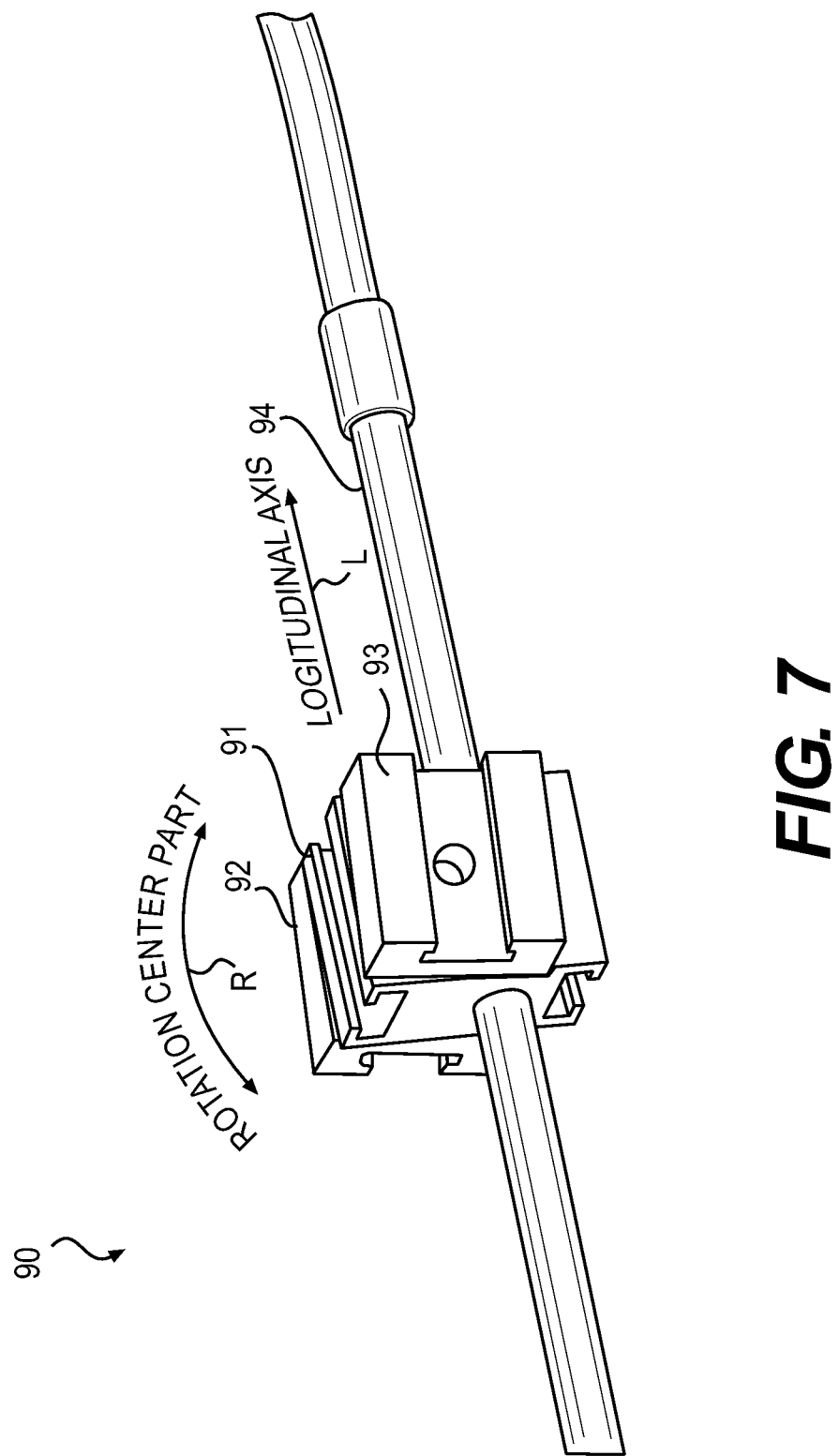
FIG. 7 presents in a schematic way a further embodiment of the modular applicator according to the invention.

FIG. 7 presents in a schematic way a further embodiment of the modular applicator according to the invention. In this embodiment, for clarity reasons, a fragment 90 of the applicator is depicted. In accordance with the present embodiment the core of the fixation mechanism 91 is adapted with two lateral elements 92, 93 arranged off-axis with respect to the central element 94 of the applicator. The core of the fixation mechanism 91 is rigidly affixed to the central element 94 in a desired position. For example, the core of the fixation mechanism 94 may be affixed using a snap fit connection (not shown for clarity). In this embodiment the longitudinal axis L of the central element is defined as a reference axis. The lateral elements 92, 93 are rotatively displaceable with respect to the core 91 of the fixation mechanism. Alternatively, it may be seen that the core 91 of the fixation mechanism together with the central element 94 are rotated along the rotation direction R with respect to the lateral elements 92, 93 which remain static in their coordinate system.

It is further found that it is advantageous if the peripheral elements are connectable to the fixation mechanism using snap-fit, seal ring, or bayonet joint connectors. Alternatively, the peripheral elements may be rigidly preassembled with the fixation mechanism.

While specific embodiments have been described above, it will be appreciated that the invention may be practiced otherwise than as described. For example, the applicator may be provided with a plurality of channels for accommodating the displaceable radioactive sources. The descriptions above are intended to be illustrative, not limiting. Thus, it will be apparent to one skilled in the art that modifications may be made to the invention as described in the foregoing without departing from the scope of the claims set out below.

We claim:

1. A modular brachytherapy applicator for insertion into a cavity of a patient for administering radioactive treatment, comprising:
    a central element formed of a rigid material and having a proximal end and a distal end;
    a first fixation mechanism located between the proximal end of the central element and the distal end of the central element, wherein the first fixation mechanism includes a first channel configured to receive the central element;
    an elongated peripheral element having a proximal end and a distal end;
    a second fixation mechanism located between the proximal end of the elongated peripheral element and the distal end of the elongated peripheral element, wherein the second fixation mechanism includes a second channel configured to receive the peripheral element;
    a connecting portion located at a proximal region of at least one of the central element and the peripheral element for connecting the brachytherapy applicator to a delivery device to receive the radioactive treatment from the delivery device; and
    a conduit extending from the connecting portion along a length of at least one of the central element and the peripheral element for containing the radioactive treatment received from the delivery device;
    wherein the central element and the peripheral element are dimensioned for insertion into the cavity of the patient,
    wherein the first fixation mechanism includes a plurality of first surfaces each configured to slidably connect with the second fixation mechanism so that the second fixation mechanism connects to the first fixation mechanism at any one of the plurality of first surfaces to allow the peripheral element to removeably attach to the central element at a plurality of positions relative to the first fixation mechanism depending on which of the plurality of first surfaces the second fixation mechanism is connected to,
    wherein the second fixation mechanism includes a second surface configured to slidably connect to one of the plurality of first surfaces, and
    wherein the second surface is shaped to interlock with the one of the plurality of first surfaces to prevent the second fixation mechanism from rotating with respect to the one of the plurality of first surfaces whenever the second surface is slidably connected to the one of the plurality of first surfaces.

2. The applicator according to claim 1, wherein a slot is located on one of the first fixation mechanism or the second fixation mechanism and a complimentary ridge is located on the other of the first fixation mechanism or the second fixation mechanism, wherein the ridge is dimensioned to fit within the slot.

3. The applicator according to claim 1, wherein a male connector is located on either of the first fixation mechanism or the second fixation mechanism and a complimentary female connector is located on the other of the first fixation mechanism or the second fixation mechanism, wherein the male connector is dimensioned to be received within the female connector.

4. The applicator according to claim 3, wherein the male connector and the female connector snap-fit with each other.

5. The applicator according to claim 3, wherein the male connector and the female connector form a bayonet joint.

6. The applicator according to claim 1, wherein the first and second fixation mechanisms are configured to connect via a seal ring.

7. The applicator according to claim 1, wherein the first fixation mechanism is configured to be rigidly connected to the second fixation mechanism.

8. The applicator according to claim 1, wherein the first fixation mechanism is configured to be moveably connected to the second fixation mechanism.

9. The applicator according to claim 1, including a plurality of peripheral elements each having a second fixation mechanism located between the proximal end and the distal end.

10. The applicator according to claim 9, wherein each of the plurality of peripheral elements is interchangeably affixable to the central element via the plurality of second fixation mechanisms.

11. The applicator according to claim 9, wherein the first fixation mechanism is configured to affix at least two of the plurality of peripheral elements to the central element at once by connecting one of the plurality of second fixation mechanisms to each of at least two of the plurality of surfaces of the first fixation mechanism at once.

12. The applicator according to claim 1, wherein the conduit is located within the central element and extends parallel to an axis of the central element.

13. The applicator according to claim 1, including a plurality of conduits.

14. The applicator according to claim 1, further comprising a sleeve dimensioned for insertion within the cavity of the patient, wherein the sleeve includes:
    a proximal end;
    a distal end;

an opening in the proximal end;

a hollow, interior region extending along a majority of a length of the sleeve from the opening in the proximal end to a distal region, wherein the interior region is dimensioned to receive at least one of the central element and the peripheral element for mounting the sleeve on at least one of the central element and the peripheral element; and an exterior surface configured to contact the cavity of the patient.

15. The applicator according to claim 14, wherein the sleeve is dimensioned to receive both the central element and the peripheral element.

16. The applicator according to claim 14, wherein the sleeve is formed of a flexible material.

17. The applicator according to claim 14, wherein the sleeve is inflatable.

18. The applicator according to claim 14, wherein at least a portion of the sleeve is textured.

19. The applicator according to claim 14, wherein the sleeve is formed of a transparent material.

20. The applicator according to claim 14, wherein the sleeve is configured to be removably mounted on at least one of the central element and the peripheral element.

21. The applicator according to claim 14, wherein the sleeve is formed of a plurality of segments.

22. The applicator according to claim 21, wherein at least some of the plurality of segments are moveable relative to each other.

23. The applicator according to claim 22, further comprising an indicator for indicating an amount of relative movement of the segments.

24. The applicator according to claim 22, wherein the sleeve includes at least two segments moveable in at least one of a longitudinal direction or a transverse direction relative to each other.

25. The applicator according to claim 14, wherein a cross-section of the sleeve varies in at least one of size and shape along an axis of the sleeve.

26. The applicator according to claim 1, wherein a proximal region of the central element is configured to operably connect to an afterloading device.

27. The applicator according to claim 1, wherein at least one of the central element and the peripheral element is tubular shaped.

28. The applicator according to claim 1, wherein the central element includes an inter-uterine tube.

29. The applicator according to claim 1, wherein the first fixation mechanism includes one or more lateral elements, at least some of the plurality of first surfaces being located on the one or more lateral elements, wherein the one or more lateral elements are rotatable with respect to a portion of the first fixation mechanism that includes the first channel configured to receive the central element.

30. The applicator according to claim 1, further comprising an elongated distal element and a distal fixation mechanism, wherein the distal fixation mechanism removeably affixes the distal element to the distal end of the central element so that the distal element projects out from the applicator parallel with an axis of the central element.

31. The applicator according to claim 30, wherein the distal element includes an inter-uterine tube.

32. A kit for building a modular brachytherapy applicator for insertion into a cavity of a patient for administering radioactive treatment, the kit comprising:

an elongated central element formed of a rigid material and having a proximal end and a distal end;

a plurality of elongated peripheral elements each having a proximal end and a distal end;

a connecting portion located at a proximal region of at least one of the central element and each of the plurality of peripheral elements, wherein the connecting portion is dimensioned to couple the applicator to a catheter to receive the radioactive treatment from the catheter;

a conduit extending from the connecting portion along a length of at least one of the central element and each of the plurality of peripheral elements for containing the radioactive treatment received from the catheter;

a first fixation mechanism located along the length of the central element, wherein the first fixation mechanism has a plurality of fixation points; and a plurality of complimentary second fixation mechanisms, wherein each peripheral element includes a second fixation mechanism located along its length, wherein each of the plurality of fixation points is dimensioned to interlock with each of the plurality of second fixation mechanisms to interchangeably affix the plurality of peripheral elements to the central element so that, when affixed, the plurality of peripheral elements are maintained at a predetermined distance from the central element and from each other, wherein each of the plurality of second fixation mechanisms includes a surface shaped to interlock with one of the plurality of fixation points to prevent the second fixation mechanism from rotating with respect to the one of the plurality of fixation points whenever the surface is interlocked with the one of the plurality of fixation points, wherein the central element and the plurality of peripheral elements are dimensioned for insertion into the cavity of the patient, and wherein each of the plurality of peripheral elements is configured to be interchangeably attached to the central element to form a modular brachytherapy applicator capable of having a plurality of different configurations depending on which of the plurality of peripheral elements is affixed to the central element and which of the plurality of fixation points on the first fixation mechanism the second fixation mechanism is attached to.

33. The kit according to claim 32, wherein the first fixation mechanism is configured to affix at least two of the plurality of peripheral elements to the central element at once by allowing at least two second fixation mechanisms to interlock with at least two fixation points at once.

* * * * *